United States Patent
Cass et al.

(10) Patent No.: US 11,439,580 B2
(45) Date of Patent: *Sep. 13, 2022

(54) EPILATORY COMPOSITIONS

(71) Applicant: Reckitt Benckiser Health Limited, Slough (GB)

(72) Inventors: Terry Alan Cass, Hull (GB); Victoria Mary Morris-Curtis, Hull (GB); Alice Heather Pope, Hull (GB)

(73) Assignee: Reckitt Benckiser Health Limited, Slough (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/075,758

(22) Filed: Oct. 21, 2020

(65) Prior Publication Data

US 2021/0069090 A1    Mar. 11, 2021

Related U.S. Application Data

(63) Continuation of application No. 15/558,760, filed as application No. PCT/GB2016/050794 on Mar. 22, 2016, now abandoned.

(30) Foreign Application Priority Data

Mar. 23, 2015 (GB) ..................... 1504855

(51) Int. Cl.
| | |
|---|---|
| A61Q 9/00 | (2006.01) |
| A61K 8/92 | (2006.01) |
| A61K 8/81 | (2006.01) |
| A61K 8/25 | (2006.01) |
| A61Q 9/04 | (2006.01) |
| A61K 8/31 | (2006.01) |

(52) U.S. Cl.
CPC .............. *A61K 8/8117* (2013.01); *A61K 8/25* (2013.01); *A61K 8/31* (2013.01); *A61K 8/8111* (2013.01); *A61K 8/92* (2013.01); *A61Q 9/04* (2013.01)

(58) Field of Classification Search
None
See application file for complete search history.

(56) References Cited

U.S. PATENT DOCUMENTS

| | | | |
|---|---|---|---|
| 8,038,723 B2 * | 10/2011 | Ellis ..................... | A61K 8/8111 8/94.16 |
| 2004/0219118 A1 * | 11/2004 | Slavtcheff ............... | A61K 8/31 424/70.1 |
| 2008/0118457 A1 * | 5/2008 | Acher ...................... | A61K 8/31 424/73 |
| 2010/0021411 A1 | 1/2010 | Bosch et al. | |

FOREIGN PATENT DOCUMENTS

| | | |
|---|---|---|
| GB | 2446576 A | 8/2008 |
| GB | 2501536 A | 10/2013 |
| WO | 2005112876 A1 | 12/2005 |
| WO | 2014198985 A1 | 12/2014 |

OTHER PUBLICATIONS

International Search Report and Written Opinion issued in International Application No. PCT/GB2016/050794 dated May 12, 2016.
International Search Report and Written Opinion issued in International Application No. PCT/GB2016/050793 dated May 24, 2016.
Combined Search and Examination Report issued in GB Application No. GB 1504850.7 dated Dec. 2, 2015.

* cited by examiner

*Primary Examiner* — Nissa M Westerberg
(74) *Attorney, Agent, or Firm* — Troutman Pepper Hamilton Sanders LLP; Ryan A. Schneider; Chris N. Davis

(57) ABSTRACT

The present invention provides an epilatory composition comprising an admixture of a hydrocarbon resin material and a mineral oil in weight ratio of 1.3:1 to 2.8:1, particulate silica, and, a polyethylene in the form of a homopolymer. An advantage of the compositions of the present invention is that they are able to provide good 'grip' to the hair to be removed and so provide for effective hair removal properties.

20 Claims, 1 Drawing Sheet

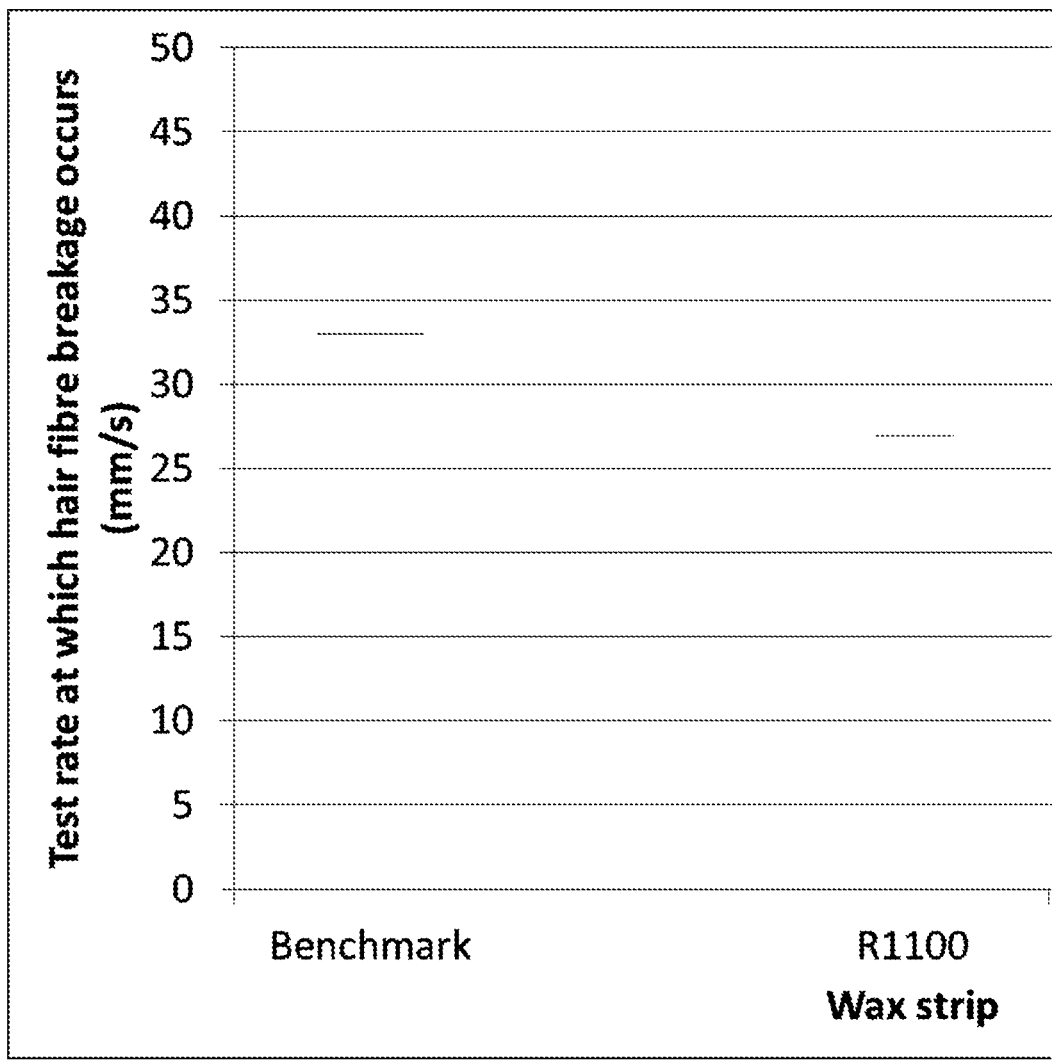

EPILATORY COMPOSITIONS

CROSS-REFERENCE TO RELATED APPLICATIONS

This application is a continuation of U.S. patent application Ser. No. 15/558,760, filed 15 Sep. 2017, which is a National Stage Entry of PCT Application No. PCT/GB2016/050794, filed 22 Mar. 2016, which claims priority to GB Application No. GB1504855.6, filed 23 Mar. 2015, the disclosures of all of which are herein incorporated by reference in their entirety.

BACKGROUND

The present invention relates to an epilatory composition and its use.

BRIEF SUMMARY OF INVENTION

In one aspect, the invention is directed to an epilatory composition comprising a hydrocarbon resin; a mineral oil; particulate silica; and a polyethylene in the form of a homopolymer, wherein the hydrocarbon resin and the mineral oil are present in the composition in a weight ratio in the range of from 1.3:1 to 2.8:1.

In another aspect, the invention is directed to an epilatory composition comprising 64-66 wt % of a hydrogenated styrene/methyl styrene/indene copolymer; 31-33 wt % of a mineral oil; 1-2 wt % of a particulate silica; and 0.8-1.2 wt % of a polyethylene in the form of a linear homopolymer, wherein the ratio of the hydrogenated styrene/methyl styrene/indene copolymer to the mineral oil is in the range of from 1.9:1 to 1.95:1.

In another aspect, the invention is directed to an epilatory composition consisting essentially of 60-68.5 wt % of a hydrogenated styrene/methyl styrene/indene copolymer; 30-38.5 wt % of a mineral oil; 1-2 wt % of a particulate silica; and 0.5-1.5 wt % of a polyethylene in the form of a linear homopolymer.

In another aspect, the invention is directed to an epilatory composition comprising: 63-66 wt % of a hydrogenated styrene/methyl styrene/indene copolymer; 31-33 wt % of a mineral oil; 1-2 wt % of particulate silica; and 0.75-1.5 wt % of a polyethylene in the form of a linear homopolymer.

In another aspect, the invention is directed to an epilatory composition comprising: 63-66 wt % of a hydrogenated styrene/methyl styrene/indene copolymer; 32-34 wt % of a mineral oil; 1-2 wt % of particulate silica; and 0.7-1.5 wt % of a polyethylene in the form of a linear homopolymer.

In another aspect, the invention is directed to an epilatory composition comprising: 63-66 wt % of a hydrogenated styrene/methyl styrene/indene copolymer; 31-33 wt % of a mineral oil; 1-2 wt % of particulate silica; and 0.8-1.2 wt % of a polyethylene in the form of a linear homopolymer.

BRIEF DESCRIPTION OF THE DRAWING

The accompanying FIGURE, which is incorporated in and constitute a part of this specification, illustrates several aspects described below.

The FIGURE shows a comparison between the fibre removal speed of an example composition of the present invention (R1100) and an example composition of the prior art (benchmark).

DETAILED DESCRIPTION

Epilatory compositions formed of viscoelastic materials are well known. The viscoelastic materials may in certain embodiments be rosin-based. In other embodiments they may be sugar-based. A tackifier, such as colophony, may be included to make them sticky.

In some products the epilatory compositions may be supplied in the form of strips, retained between cellophane or woven sheets. The cellophane sheets may have coatings of polyvinyl chloride, which acts as a barrier preventing the composition, or components of it, from migrating through the sheets; and also having the correct adhesive properties for use. In use, the user peels away one of the cellophane sheets, presses the epilatory strip firmly onto the area to be plucked, then pulls one end of the remaining sheet sharply away from the area. The hairs trapped in the composition are removed from the treated area along with, optimally, all of the composition, still attached to the remaining backing strip.

In an alternative approach a composition may be warmed, and then applied to the skin by means of a spatula or other applicator. Strips of fabric are then applied so that they adhere to the epilatory composition. The strips are then pulled sharply to remove the epilatory material, and hair, from the skin.

In both approaches the viscoelastic properties of the compositions are important. However this is particularly so in the case of the compositions supplied as strips, since these are applied to the skin at ambient temperature. At ambient temperature the compositions should be soft and pliable, such that they mould closely to the body shape. On the other hand they must not be so soft that they flow prior to use. When they are in place on the body and the user pulls the remaining backing strip, applying a high frequency strain rate to the compositions, their elastic properties should predominate over their viscous properties.

There is a need for an epilatory composition having an improved 'grip' of the user's hair thus leading to more efficient hair removal. In current compositions the 'grip' of the wax is sub-optimal and as a result care must be taken when removing the wax to ensure maximum efficacy.

In accordance with the present invention there is provided an epilatory composition comprising an admixture of a hydrocarbon resin material and a mineral oil in weight ratio of 1.3:1 to 2.8:1, particulate silica, and a polyethylene in the form of a homopolymer.

Preferably the ratio of hydrocarbon resin to mineral oil is 1.5:1 to 2.3:1. More preferably the ratio is 1.9:1 to 2.2:1. Most preferably the ratio is 1.9:1 to 1.95:1.

Preferably, however, the hydrocarbon resin is selected from poly(methylstyrene-co-indene), hydrogenated polycyclopentadiene resin, $C_5$-$C_9$ partially or fully hydrogenated hydrocarbon resin, hydrogenated styrene/methyl styrene/indene copolymer. A more preferred resin is hydrogenated styrene/methyl styrene/indene copolymer.

Preferably the epilatory composition comprises from 55-70% wt/wt of hydrocarbon resin material, preferably from 63-68% wt/wt, more preferably 64-66% wt/wt.

DETAILED DESCRIPTION OF INVENTION

The epilatory composition can comprise an oil selected from the group consisting of mineral oils, argan oils and castor oils. A preferred mineral oil is paraffin oil.

Typically, the composition comprises 25-40% wt/wt of the mineral oil. More typically the amount is 30-35% wt/wt. More typically, the amount is 32-34% wt/wt.

The addition of a polyethylene in the form of a homopolymer to an epilatory composition with a resin mix and silica substantially improves the hair removal efficacy of the composition when compared to other polymers known in the art, for example polyisobutane or $C_{1-4}$ polyalkylene. The efficacy is especially improved when the epilatory formulation is in a cold wax strip format. It has also been observed to improve the stability of the wax on strips, and the resistance to flow under warm conditions.

Preferably the polyethylene has a molecular weight from 100 to 1000, preferably from 250 to 800 more preferably from 300 to 600 unified mass units. This gives the advantage of ease of incorporation of the polyethylene into the hydrophobic particles of the invention by melting and blending. Polyethylene suitable for use in compositions of the invention is a substantially linear or non-branched polymer with the structure $CH_3CH_2(CH_2CH_2)_nCH_2\ CH_3$, where n is a mean number from 5 to 35, preferably from 8 to 15. Preferably at least 90% by weight of the polyethylene is linear or non-branched. A particularly preferred polyethylene is that sold under the registered trade name Performalene. Other suitable polymers include polybutene grades, ethylene and vinyl acetate, goovean fibre viscose, however performalene is preferred.

The polyethylene is typically present in an amount in the range 0.1% to 5% by weight of the composition. Preferably, 0.5% to 4.0%, more preferably 0.5% to 3.0% by weight of the composition. However, a particularly preferred amount is in the range 0.75% to 1.5%, such as around 1.0% by weight of the composition.

It is desirable that the ratio of the silica to polyethylene is in the range 16:1 to 2:3. Preferably the ratio of silica to polymer or co-polymer is in the range 6:1 to 6:5. A particularly preferred ratio is in the range 2:1.

The matrix material is suitably a gel-like material with adhesive properties.

The epilatory composition can be used in any suitable form such as a hot wax, a cold wax or as part of a cold wax strip. Preferably the epilatory composition is a so-called "cold" epilatory composition (that is, one which can be applied at ambient temperature without reheating).

Typically, the particulate silica is fumed silica. Preferably the particulate fumed silica is a colloidal material. Preferably it has particles of mean diameter 1-200 nm, more preferably 5-100 nm, and most preferably 10-50 nm.

Preferably the particles are present in the matrix material in an amount of at least 0.5% wt/wt, more preferably at least 1.0% wt/wt, and most preferably at least 1.5% wt/wt. Suitably they are present in an amount up to 10% wt/wt, preferably up to 8.0% wt/wt, and most preferably up to 6.0% wt/wt. It is particularly preferred that the particulate silica is present in an amount substantially about 2.0% by weight of the formulation.

Fumed silica is currently manufactured in a process that involves flame hydrolysis of silicon tetrachloride, in an oxy-hydrogen flame. It is a colloidal form of silica having silanol groups, able to participate in hydrogen bonding. Fumed silica typically comprises colloidal particles of mean diameter 1-200 nm. Preferably the fumed silica is of mean diameter 5-100 nm, more preferably 10-50 nm. The external surface area is typically in the range 15-380 $m^2/g$. Fumed silicas are typically non-porous and thus have no internal surface area. They may be hydrophobic and of use in the present invention but preferred fumed silicas for use in the present invention are hydrophilic.

The epilatory composition may suitably comprise up to 40%, preferably up to 20%, of other components, which may include one or more of a natural wax, a fragrance, a polymer, an essential oil, a silicone oil, a colorant or an anti-oxidant.

In an embodiment there is provided an epilatory composition comprising:
  a. 60-68.5 wt % of a hydrocarbon resin;
  b. 30-38.5 wt % of a mineral oil;
  c. 1-2 wt % of a particulate silica; and
  d. 0.5-1 wt % of a polyethylene in the form of a linear homopolymer.

In an alternative embodiment the composition comprises:
  a. 64-66 wt % of a hydrocarbon resin;
  b. 31-33 wt % of a mineral oil;
  c. 1-2 wt % of a particulate silica; and
  d. 0.8-1.2 wt % of a polyethylene in the form of a linear homopolymer.

The composition can comprise:
  a. a hydrogenated styrene/methyl styrene/indene copolymer;
  b. a mineral oil;
  c. particulate silica; and
  d. a polyethylene in the form of a linear homopolymer
  wherein the ratio of the resin to paraffin oil is 1.9:1 to 1.95:1.

In an alternative embodiment the composition consists essentially of
  a. 60-68.5 wt % of a hydrogenated styrene/methyl styrene/indene copolymer;
  b. 30-38.5 wt % of a mineral oil;
  c. 1-2 wt % of a particulate silica; and
  d. 0.5-1.5 wt % of a polyethylene in the form of a linear homopolymer.

In an alternative preferred embodiment the composition consists essentially of
  a. 64-66 wt % of a hydrogenated styrene/methyl styrene/indene copolymer;
  b. 31-33 wt % of a mineral oil;
  c. 1-2 wt % of particulate silica; and
  d. 0.8-1.2 wt % of a polyethylene in the form of a linear homopolymer.

In a more preferred embodiment the composition consists of
  a. 60-68.5% of a hydrogenated styrene/methyl styrene/indene copolymer;
  b. 30-38.5% of a paraffin oil;
  c. 1-2% of particulate silica;
  d. 0.5-1.5 wt % of a polyethylene in the form of a linear homopolymer;
  e. 0.1% of shea butter; and
  f. 0.6-0.65% of a fragrance.

In an alternative more preferred embodiment the composition consists of
  a. 64-66% of a hydrogenated styrene/methyl styrene/indene copolymer;
  b. 31-33% of a paraffin oil;
  c. 1-2% of particulate silica;
  d. 0.5-1.5 wt % of a polyethylene in the form of a linear homopolymer;
  e. 0.1% of shea butter; and
  f. 0.6-0.65% of a fragrance.

Suitably an epilatory composition comprising a hydrocarbon resin material, when formed into sheets and not under applied stress, is shape-stable for a period of 6 months at all temperatures in the range 20-50° C.

Suitably an epilatory composition comprising a hydrocarbon resin material, when formed into sheets and not under applied stress, is shape-stable for a period of 6 months at all temperatures in the range 20-50° C.; whereas the corresponding matrix material not containing any said particles, when formed into flat sheets and not under applied stress, flows under its own weight at least some temperatures in the range 20-50° C. during a period of 6 months.

Suitably the epilatory composition is such that its elastic modulus exceeds its viscous modulus at all frequencies up to 0.1 rad/s at 50° C.

Preferably the elastic modulus of the epilatory composition exceeds its viscous modulus at all frequencies up to 1 rad/s at 50° C., more preferably at all frequencies up to 2 rad/s at 50° C.

Preferably at certain higher frequencies (representative of the rapid removal of the epilatory composition from the user's skin), the elastic modulus also exceeds the viscous modulus, at temperatures within the temperature range 20-50° C.

Preferably the elastic modulus exceeds the viscous modulus (when measured at 35° C.) at a frequency of at least 10,000 rad/s, more preferably at a frequency at least 5,000 rad/s.

Thus, preferably the epilatory composition is such that, at ambient temperatures, at low frequencies of applied stress the elastic modulus exceeds the viscous modulus; at high frequencies of applied stress the elastic modulus exceeds the viscous modulus; and at moderate frequencies, in between, the viscous modulus exceeds the elastic modulus. The epilatory composition in transit and storage corresponds to the low frequency condition, and the non-viscous nature of the composition aids shape stability in storage and transit; the application of the epilatory composition to the skin corresponds to the moderate frequency condition, and the viscous nature of the composition aids application and good contact with hair and skin; and pulling the epilatory composition sharply from the skin corresponds to the high frequency condition, the non-viscous, glassy nature of the composition aiding effective hair removal. The transition between the low frequency condition and the moderate frequency condition is known as the gel point. The transition between the moderate frequency condition and the high strain rate condition is known as the glass transition.

The elastic modulus G' (sometimes known as the storage modulus) corresponds to the energy which can be stored and released by a bulk material. The viscous modulus G" (sometimes known as the loss modulus) corresponds to the energy dissipated by a bulk material due to friction between its macromolecules when it is deformed.

$$G' = \frac{\sigma_o}{\gamma_o} \cos \delta$$
$$G'' = \frac{\sigma_o}{\gamma_o} \sin \delta$$

wherein σ. is the stress amplitude, γ. is the strain amplitude and δ is the out-of-phase coefficient.

The measurements quoted later are based on studies carried out into the rheology of the viscoelastic compositions in order to obtain a better understanding of their adhesive behaviour and their suitability as epilatory materials. These studies involved subjecting the materials to dynamic investigations in which a sinusoidal strain at defined frequencies was applied to the materials and the resulting output force was measured. In these studies a stress control rheometer was used, the SR rheometer commercially available from the company Rheometrics, using parallel plate geometry of 25 mm in diameter. The output force was found to include an in-phase elastic component G' and an out-of-phase viscous component G". The output force can be expressed as follows.

$$\sigma = \sigma_o \sin(t\omega + \delta)$$
$$= \sigma_o \cos\delta \sin t\omega + \sigma_o \cos\delta \cos t\omega$$

where ω is the test frequency and t is the time.

Within the linear stress-strain domain of the material G' is desirably lower than G" at moderate frequency oscillation in order to prevent the material cracking and to ensure that the material has strong adhesion at the material/hair interface. The values of G' and G" at moderate frequency oscillation are a measure of how readily the material wets the hairs. Moderate frequency oscillation is a long time process and corresponds to the time when the material is being applied to the skin. The lower values of G' and G" at this moderate frequency, the better the material wets the hairs. Thus the hairs become well embedded in the material in a very short time (ie the time needed for spreading the material on the skin). However G' should be higher than G" at high frequency oscillation (which mimics the action of the user in rapidly pulling the strip from the body) in order to remove hairs efficiently. Also, at low frequency oscillation, or no oscillation, G' is preferably higher than G", in accordance with this invention, in order to obtain the benefit of enhanced stability, even when warm.

The definitions given herein refer to stresses applied to the material within its linear stress-strain domain, which may typically be up to a few thousand Pa.

By ensuring that the epilatory composition satisfies the above parameters, it can be readily applied to the skin at body temperature, yet it is very efficient at removing hairs from the skin and, surprisingly, the user experiences less pain.

References in this specification to a material not under applied stress are to a material in the form of a flat sheet, resting on a horizontal surface.

Whilst we are not bound by any theory, we believe that the composition of the present invention has increased efficacy as a result of an improvement in the coating of the individual's hair.

If wished the epilatory composition of the present invention may be provided in a container, from which the user removes it using, for example, a spatula or an applicator fitted to the container, and applies it to the skin. A fabric can then be used to pull the applied material in one piece from the skin. Alternatively, and preferably, the epilatory composition is supplied in the form of strips, sandwiched between sheets, for example of cellophane, or paper or another non-woven material. In use, one sheet is removed from a strip of epilatory composition and that strip is then applied to the skin with the remaining sheet uppermost. The end of that sheet is grasped and pulled sharply, to remove the strip of epilatory composition from the skin, along with hairs with which it is in contact.

In accordance with a further aspect there is provided an epilatory product, comprising epilatory strips formed of an epilatory composition as defined herein, the epilatory strips being sandwiched between sheets which are peelable from the strips.

In accordance with a further aspect there is provided a method of epilation, using a composition or product of the invention.

The invention will now be further described, by way of example with reference to the accompanying FIGURE which illustrates fibre removal speeds of compositions of the present application.

Example 1

| Standard Name | Function | Percentage |
| --- | --- | --- |
| Petroleum Hydrocarbon Resin | Epilatory Agent | 64.5116 |
| White Mineral Oil | Solvent | 31.7744 |
| Fumed Silica | Rheology Modifier | 2.0000 |
| Polyethylene | Rheology Modifier | 1.0000 |
| Shea Butter | Cosmetic Active | 0.1000 |
| Fragrance | Fragrance | 0.6140 |
| Total | | 100.00 |

The formulation can be made in the following way:

The mineral oil is heated to about 100° C. at which point the resin is added slowly with stirring to form a uniform mixture. Polyethylene is then added with stirring until a homogeneous mixture is formed. Silica is added and stirred until homogenous. Shea butter and premix are then added and the resulting mixture is left to cool for 24 hours. At that time the wax is heated until free flowing and subsequently homogenized.

The FIGURE illustrates a graph that plots the fibre removal speed of an example composition of the present invention (R1100) and an example composition of the prior art (benchmark).

As can be seen the required removal speed for the example of the present application is significantly slower than that of the prior art. From this it can be concluded that the compositions of the present application have improved grip over the prior art.

An advantage of the present invention is that there is provided an epilatory composition having improved grip of a user's hair such that the composition having a more efficacious mode of action.

A further advantage of the compositions of the present invention is that as a result of their improved grip/adherence the compositions can be used more quickly than those compositions which have poorer grip/adherence thus requiring a longer period of time to become effective.

Further modifications and improvements can be made without departing from the scope of the invention described herein.

What is claimed is:

1. An epilatory composition comprising:
   63-66 wt % of a hydrogenated styrene/methyl styrene/indene copolymer;
   31-33 wt % of a mineral oil;
   1-2 wt % of particulate silica; and
   0.75-1.5 wt % of a polyethylene in the form of a linear homopolymer.

2. An epilatory composition comprising:
   63-66 wt % of a hydrogenated styrene/methyl styrene/indene copolymer;
   32-34 wt % of a mineral oil;
   1-2 wt % of particulate silica; and
   0.7-1.5 wt % of a polyethylene in the form of a linear homopolymer.

3. An epilatory composition comprising:
   63-66 wt % of a hydrogenated styrene/methyl styrene/indene copolymer;
   31-33 wt % of a mineral oil;
   1-2 wt % of particulate silica; and
   0.8-1.2 wt % of a polyethylene in the form of a linear homopolymer.

4. The epilatory composition as claimed in claim 1, wherein the polyethylene has a molecular weight from 100 to 1000 unified mass units.

5. The epilatory composition as claimed in claim 2, wherein the polyethylene has a molecular weight from 100 to 1000 unified mass units.

6. The epilatory composition as claimed in claim 3, wherein the polyethylene has a molecular weight from 100 to 1000 unified mass units.

7. The epilatory composition as claimed in claim 1, wherein the hydrogenated styrene/methyl styrene/indene copolymer is present in an amount of about 63% to about 64% by weight of the composition.

8. The epilatory composition as claimed in claim 2, wherein the hydrogenated styrene/methyl styrene/indene copolymer is present in an amount of about 63% to about 64% by weight of the composition.

9. The epilatory composition as claimed in claim 3, wherein the hydrogenated styrene/methyl styrene/indene copolymer is present in an amount of about 63% to about 64% by weight of the composition.

10. The epilatory composition as claimed in claim 1, wherein the mineral oil is present in an amount of about 32% to about 33% by weight of the composition.

11. The epilatory composition as claimed in claim 2, wherein the mineral oil is present in an amount of about 32% to about 33% by weight of the composition.

12. The epilatory composition as claimed in claim 3, wherein the mineral oil is present in an amount of about 32% to about 33% by weight of the composition.

13. The epilatory composition as claimed in claim 1, wherein the particulate silica is present in an amount of about 2.0% by weight of the composition.

14. The epilatory composition as claimed in claim 2, wherein the particulate silica is present in an amount of about 2.0% by weight of the composition.

15. The epilatory composition as claimed in claim 3, wherein the particulate silica is present in an amount of about 2.0% by weight of the composition.

16. The epilatory composition as claimed in claim 1, wherein the mineral oil is a paraffin oil.

17. The epilatory composition as claimed in claim 2, wherein the mineral oil is a paraffin oil.

18. The epilatory composition as claimed in claim 3, wherein the mineral oil is a paraffin oil.

19. The epilatory composition as claimed in claim 1, wherein the polyethylene is present in an amount of about 1.0% by weight of the composition.

20. The epilatory composition as claimed in claim 2, wherein the polyethylene is present in an amount of about 1.0% by weight of the composition.

* * * * *